US006202230B1

(12) United States Patent
Borders

(10) Patent No.: US 6,202,230 B1
(45) Date of Patent: Mar. 20, 2001

(54) SURGICAL TABLE APPARATUS

(75) Inventor: Richard L. Borders, Cincinnati, OH (US)

(73) Assignee: Hill-Rom, Inc., Batesville, IN (US)

( * ) Notice: Subject to any disclaimer, the term of this patent is extended or adjusted under 35 U.S.C. 154(b) by 0 days.

(21) Appl. No.: 09/187,990

(22) Filed: Nov. 6, 1998

Related U.S. Application Data

(60) Provisional application No. 60/064,709, filed on Nov. 7, 1997, and provisional application No. 60/083,673, filed on Apr. 30, 1998.

(51) Int. Cl.[7] .............................. A61G 13/00; A61G 13/12
(52) U.S. Cl. .......................... 5/618; 5/613; 5/619; 5/624
(58) Field of Search ............................... 5/600, 610, 613, 5/614, 618, 619, 624, 648, 650, 651

(56) References Cited

U.S. PATENT DOCUMENTS

| 12,944 | 5/1855 | Daniels . | |
|---|---|---|---|
| 238,799 | * 3/1881 | Morgan | 5/619 |
| 1,437,568 | 12/1922 | Taplin . | |
| 1,626,091 | 4/1927 | Macklin . | |
| 1,775,547 | * 9/1930 | Bayer | 5/619 X |
| 2,042,399 | 5/1936 | Holme . | |
| 2,258,782 | 10/1941 | McKean . | |
| 2,872,259 | * 2/1959 | Thorpe | 5/624 X |
| 2,972,505 | 2/1961 | Weickgenannt . | |
| 3,041,121 | 6/1962 | Comper . | |
| 3,041,122 | * 6/1962 | Weickgenannt et al. | 5/618 X |
| 3,227,440 | 1/1966 | Scott . | |
| 3,281,141 | * 10/1966 | Smiley et al. | 5/618 X |
| 3,318,596 | * 5/1967 | Herzog | 5/619 |
| 3,411,766 | 11/1968 | Lanigan . | |
| 3,754,749 | * 8/1973 | Lyon et al. | 5/618 |
| 3,868,103 | 2/1975 | Pageot et al. . | |

(List continued on next page.)

FOREIGN PATENT DOCUMENTS

| 1258021 | 1/1968 | (DE) . |
|---|---|---|
| 1518724 | 3/1968 | (FR) . |
| 2 547 195 | 12/1984 | (FR) . |
| 1058787 | 2/1967 | (GB) . |
| 42-11267 | 9/1960 | (JP) . |
| 42-1715 | 9/1960 | (JP) . |
| 35-19293 | 8/1961 | (JP) . |
| 35-28580 | 10/1961 | (JP) . |
| 39-32275 | 10/1965 | (JP) . |
| 40-23833 | 10/1966 | (JP) . |
| 46-21835 | 7/1971 | (JP) . |
| 52-7276 | 3/1977 | (JP) . |
| 53-74190 | 6/1978 | (JP) . |
| 53-74191 | 6/1978 | (JP) . |
| 58-127648 | 7/1983 | (JP) . |
| 58-143753 | 8/1983 | (JP) . |
| 61-226043 | 10/1986 | (JP) . |

OTHER PUBLICATIONS

Midmark Corporation, 547 SLS™ brochure, 4 pages, Feb. 1998.

Hausted, "Models 878, 678 & 675 Uni–Care® Mobile Surgical Stretcher", date unknown, 1 page.

Koenigkramer Dentsply, "Reliance® M–701 Surgical Stretcher", date unknown, 2 pages.

Stryker, "Head/Neck Surgery Stretcher Model 1067", 1992, 2 pages.

Hausted, "Products for Head and Neck Surgery", date unknown, 4 pages.

Primary Examiner—Terry Lee Melius
Assistant Examiner—Robert G. Santos
(74) Attorney, Agent, or Firm—Bose McKinney & Evans LLP

(57) ABSTRACT

A surgical table apparatus includes a base, a pedestal, and an upper support frame coupled to the pedestal. The upper support frame includes a head frame section, a seat frame section, optional leg supports, and optional head supports.

52 Claims, 9 Drawing Sheets

U.S. PATENT DOCUMENTS

| | | |
|---|---|---|
| 3,929,309 | 12/1975 | De Vore . |
| 3,967,128 * | 6/1976 | Smulewicz ............................ 5/601 X |
| 4,103,170 * | 7/1978 | Spradlin ............................... 5/619 X |
| 4,148,472 | 4/1979 | Rais et al. . |
| 4,247,091 | 1/1981 | Glowacki et al. . |
| 4,390,011 | 6/1983 | Evans . |
| 4,552,346 | 11/1985 | Schnelle et al. . |
| 4,559,656 * | 12/1985 | Foster ................................... 5/613 X |
| 4,592,104 * | 6/1986 | Foster et al. ......................... 5/618 X |
| 4,809,687 | 3/1989 | Allen ........................................ 5/624 |
| 4,865,303 * | 9/1989 | Hall ........................................ 5/614 |
| 4,872,656 * | 10/1989 | Brendgord et al. ...................... 5/601 |
| 4,881,728 | 11/1989 | Hunter . |
| 4,882,797 | 11/1989 | Fallor et al. . |
| 4,989,848 * | 2/1991 | Monroe ................................. 5/624 X |
| 5,135,210 | 8/1992 | Michelson . |
| 5,157,800 * | 10/1992 | Borders ................................. 5/624 X |
| 5,226,187 * | 7/1993 | Borders et al. ....................... 5/619 X |
| 5,231,719 * | 8/1993 | Schnelle .................................. 5/614 |
| 5,335,384 | 8/1994 | Foster et al. . |
| 5,369,827 | 12/1994 | Parke ................................... 5/650 X |
| 5,427,436 | 6/1995 | Lloyd . |
| 5,560,577 | 10/1996 | Keselman ............................ 5/624 X |
| 5,575,026 | 11/1996 | Way et al. . |
| 5,582,379 | 12/1996 | Keselman et al. ................ 248/279.1 |
| 5,754,997 | 5/1998 | Lüssi et al. . |
| 5,774,915 | 7/1998 | Scott et al. . |
| 5,784,734 | 7/1998 | Scott et al. . |
| 5,802,641 | 9/1998 | Van Steenburg ......................... 5/648 |
| 5,862,549 * | 1/1999 | Morton et al. ........................... 5/610 |
| 5,918,330 | 7/1999 | Navaroo et al. ........................... 5/624 |
| 5,926,878 * | 7/1999 | Morton et al. ........................... 5/624 |
| 5,941,175 | 8/1999 | Bannister ............................ 5/624 X |
| 5,961,085 | 10/1999 | Navarro et al. ...................... 5/623 X |
| 6,058,534 * | 5/2000 | Navarro et al. ........................... 5/648 |

* cited by examiner

SURGICAL TABLE APPARATUS

BACKGROUND AND SUMMARY OF THE INVENTION

This application claims the benefit of U.S. provisional application Ser. No. 60/064,709 filed Nov. 7, 1997 and U.S. provisional application Ser. No. 60/083,673 filed Apr. 30, 1998.

The present invention relates to a surgical table apparatus. More particularly, the present invention relates to improved leg support sections and head support sections for a surgical table apparatus.

The surgical table apparatus of the present invention includes a variety of upper support frame configurations configured to support a patient in many different positions during a surgical procedure. The upper support frame is configured to receive a mattress or other support surface on which the patient is positioned. The upper support frame is supported on a pedestal extending upwardly from a base. A leg support section of the upper support frame of the surgical table apparatus is either a one-piece two section leg support, a two-piece longitudinally split leg support, or a two-piece two section leg support. Each of the leg supports are designed to articulate about two transverse spaced-apart axes over a range of +/−90°. The length of each leg support is adjustable relative to the rest of the upper support frame. The pivotable leg support sections provide a wide range of positioning capabilities for positioning a patient during a surgical procedure.

The upper support frame also includes different types of optional head supports configured to support the head of a patient on the table. Each of the head supports has an adjustable length and is removable. A first optional head support is a one-piece multifunction head section. This head section is pivotable to support the patient in either a supine or prone position. The head section may be elevated relative to the remainder of the patient support surface to provide lateral support when the patient is positioned on one side or the other.

A second optional head support is a two-piece head section including inner and outer pivotable sections. The inner and outer sections may be substantially co-planar to provide full head and neck support for the patient. The outer section is pivoted downwardly to provide full neck support with head access. The inner section may be pivoted downwardly to provide airway access in a prone position. The outer section may be pivoted upwardly above the remainder of the patient support surface to provide lateral support for the patient's head when the patient is situated on one side or the other.

According to one aspect of the present invention, a surgical table apparatus includes a base and an upper support frame coupled to the base. The upper support frame includes a head frame section, a seat frame section, and first and second separate leg support sections. The first and second leg support sections each include a first frame section pivotably coupled to the seat frame section by a first joint for independent movement about a first pivot axis, and a second frame section pivotably coupled to the first frame section by a second joint for independent movement about a second pivot axis. The first and second pivot axes are transverse to a longitudinal axis of the upper support frame.

In an illustrated embodiment, the first joint of each of the first and second leg support sections includes an arm movably coupled to the seat frame section to permit a length of the first and second leg support sections to be adjusted relative to the seat frame section. In another illustrated embodiment, the seat frame section includes first and second side portions, and the first and second leg support sections are pivotable outwardly relative to the seat frame section about first and second vertical pivot axes located adjacent the first and second side portions of the seat frame section, respectively. Also in an illustrated embodiment, first and second separate mattress sections located on the first and second leg support sections, respectively.

The first frame section of each of the first and second leg support sections is pivotable relative to the seat frame section through a range of motion of +/−90° relative to the seat frame section. The second frame section of each of the first and second leg support sections is pivotable relative to the first frame section through a range of motion of +/−90°.

In one illustrated embodiment, the first joint of each of the first and second leg support sections includes a clevis pivotably coupled to the first frame section, and a coupler pivotably coupled to the clevis about a pivot axis transverse to the first pivot axis. The coupler is pivotably coupled to the seat frame section. The illustrated apparatus also includes a cylinder having a movable piston to control pivotable movement of the first frame section relative to the seat frame section. One of the cylinder and piston is pivotably coupled to the seat frame section, and the other of the cylinder and piston being pivotably coupled to the coupler.

In another illustrated embodiment, each of the first and second leg support sections includes a foot support panel pivotably coupled to the second frame section. The first and second leg support sections each also include a removable thigh support panel coupled to the first frame section. Illustratively, each foot support panel is coupled to a ball connector and each second frame section is formed to include a socket configured to receive the ball so that the foot support panel is movable relative to the second frame section. Each of the first and second leg support sections includes an actuator coupled to the second frame section to release the ball for pivotable movement relative to the second frame section. Also illustratively, each foot support panel includes a bottom plate having first and second separate sections pivotably coupled together so that the foot support panels are foldable to form generally concave calf supports.

In yet another illustrated embodiment, each second joint includes a third frame section pivotably coupled to the second frame section. The third frame section is slidably coupled to the first frame section to permit the position of the second frame section to be adjusted relative to the first frame section.

Illustratively, each of the first joints includes a latch configured to secure the first frame section to the seat frame section. The latch is releasable to permit the first and second leg support sections to be removed from the seat frame section.

According to another aspect of the present invention, a surgical table apparatus includes a base, an upper support frame coupled to the base to support a person, and a head support coupled to the upper support frame. The head support includes a first arm movably coupled to the upper support frame to permit a length of the head support to be adjusted relative to the upper support frame. The head support also includes a second arm having a first end pivotably coupled to the first arm by a first joint and a second end. The head support further includes a head support section pivotably coupled to the second end of the second arm by a second joint.

In an illustrated embodiment, the head support section includes a bottom plate pivotably coupled to the second arm and a pad located on the plate. The bottom plate includes an end edge located adjacent the upper support frame and the pad includes a portion covering the end edge of the plate. Illustratively, the portion of the pad covering the end edge of the plate is generally U-shaped.

Also in an illustrated embodiment, the upper support frame includes a support surface thereon. The second arm and the head support section are movable to an elevated position so that the head support section is located above the support surface on the upper support frame. The head support section is pivotable upwardly relative to the second arm to define an opening between the head support section and an end of the upper frame section.

According to yet another aspect of the present invention, a surgical table apparatus includes a base and an upper support frame coupled to the base. The upper support frame includes a head frame section, a seat frame section, and a leg support movably coupled to the seat frame section to permit a length of the leg support to be adjusted relative to the seat frame section. The leg support includes a first frame section pivotably coupled to the seat frame section by a first joint for movement about a first pivot axis, and a second frame section pivotably coupled to the first frame section by a second joint for movement about a second pivot axis. The first and second pivot axes are transverse to a longitudinal axis of the upper support frame.

In an illustrated embodiment, the first joint includes an arm movably coupled to the seat frame section to permit a length of the first and second leg support sections to be adjusted relative to the seat frame section. The first frame section is pivotably coupled to the arm.

The first frame section is pivotable relative to the seat frame section through a range of motion of +/−90° relative to the seat frame section. The second frame section is pivotable relative to the first frame section through a range of motion of +/−90°.

In another illustrated embodiment, the first joint includes a latch configured to secure the first frame section to the seat frame section. The latch is releasable to permit the leg support to be removed from the seat frame section.

According to still another aspect of the present invention, a surgical table apparatus includes a base, an upper support frame coupled to the base to support a person, and a head support coupled to the upper support frame. The head support includes a pair of spaced apart first arms slidably coupled to the upper support frame to permit a length of the head support to be adjusted relative to the upper support frame. The head support also includes a pair of second arms. Each second arm has a first end pivotably coupled to one of the first arms by a first joint and a second end. The head support further includes an outer head support section pivotably coupled between the second ends of the second arms by a pair of second joints, and an inner head support section coupled to one of the first and second arms by a third joint. Therefore, the inner and outer head support sections and the first and second arms are all independently movable relative to each other.

In an illustrated embodiment, the inner head support section is pivotable downwardly relative to the outer head support section to provide an opening between the outer head support section and an end of the upper support frame. The second arms and the outer head support section are pivotable upwardly so that the outer head support section is located above a support surface on the upper support frame. The outer head support section is also pivotable downwardly relative to the inner head support section so that the inner head support section is used to support the neck of the person.

In the illustrated embodiment, the outer head support section is generally U-shaped and surrounds a portion of the inner head support section. The inner head support section is coupled to a pair of posts. Each post is pivotably coupled to one of the first joints.

Additional features and advantages of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying drawings in which.

DETAILED DESCRIPTION OF THE DRAWINGS

Figure 1:
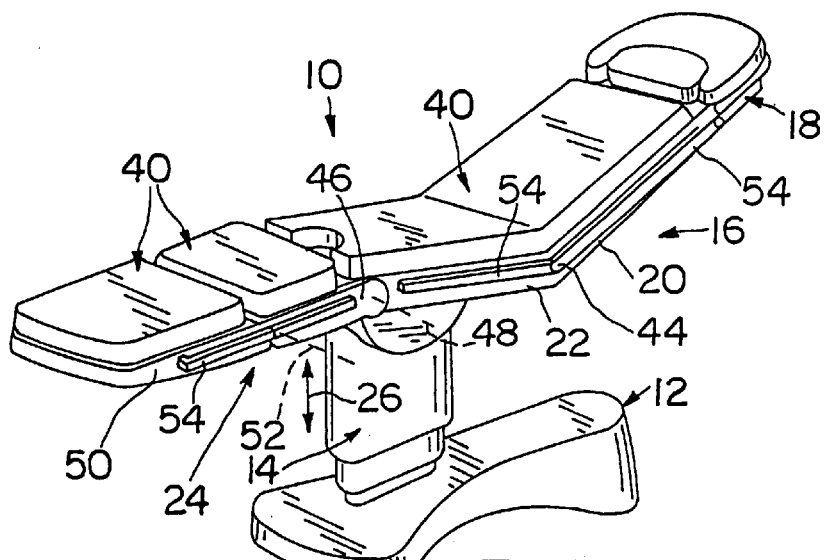
FIG. 1 is a perspective view of a first embodiment of a surgical table apparatus of the present invention including a one-piece, two section leg support.

Referring now to the drawings, FIG. 1 illustrates a first embodiment of a surgical table apparatus 10 in accordance with the present invention. The apparatus 10 includes a base 12 and a pedestal 14 coupled to the base 12. An upper support frame 16 is coupled to the pedestal 14. The upper support frame 16 includes a head section 18, a back section 20, a seat section 22, and a leg section 24. The pedestal 14 includes a hi/lo mechanism (not shown) for moving the telescoping pedestal 14 upwardly and downwardly in the direction of double-headed arrow 26 to raise and lower the upper support frame 16 relative to the ground.

Figure 2:
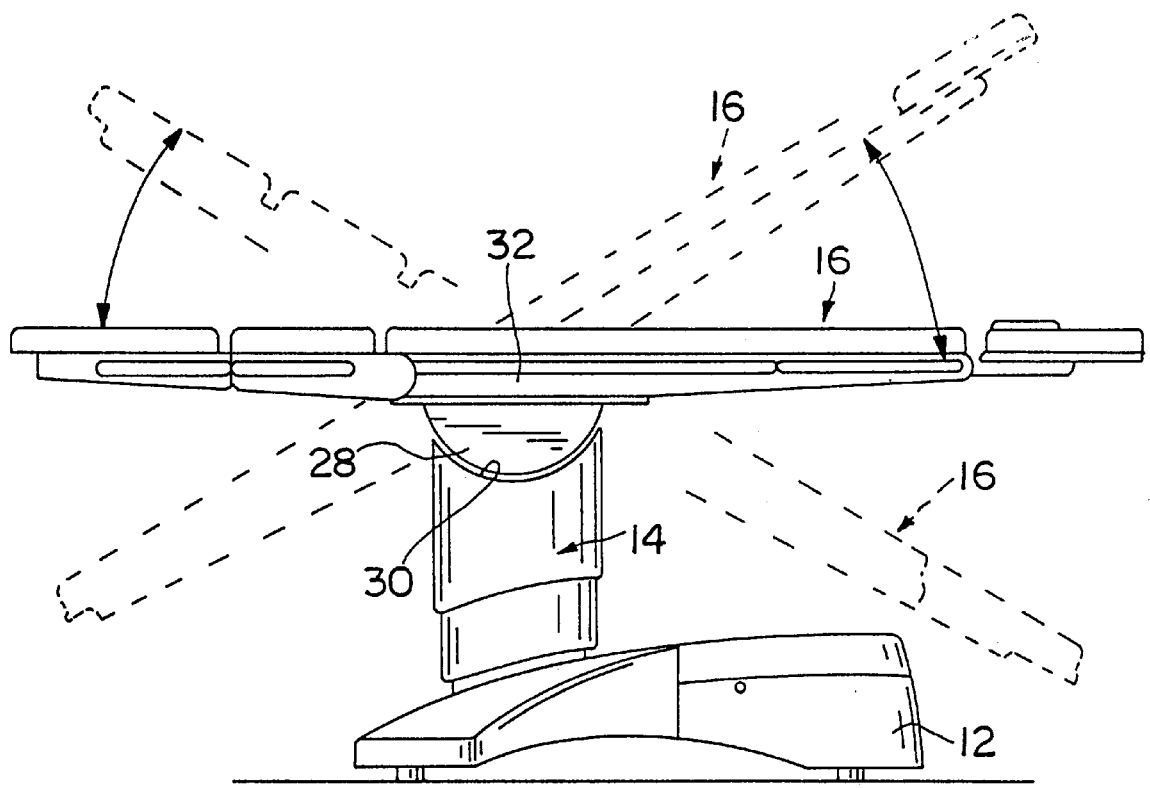
FIG. 2 is a side elevational view of the surgical table apparatus of FIG. 1 illustrating pivotal movement of an upper support frame relative to a pedestal supported on a base about an axis transverse to a longitudinal axis of the upper support frame so that the upper support frame can be moved between a Trendelenburg position and a reverse Trendelenburg position.

As illustrated in FIG. 2, the upper support frame 16 is coupled to a convex bearing surface 28 which is then coupled to a concave bearing surface 30 on the pedestal 14. A driver (not shown) such as a cylinder, gear, or other mechanism is used to provide powered pivotable movement of the upper support frame 16 about transverse pivot axis 32 in both directions to move the upper support surface 16 between a Trendelenburg position a reverse Trendelenburg position as illustrated by the dotted line positions shown in FIG. 2.

Figure 3:
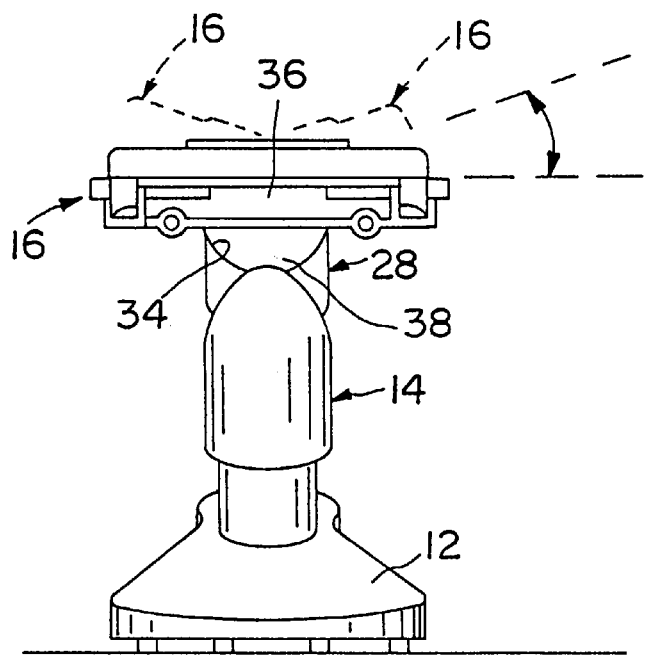
FIG. 3 is an end view of the surgical table apparatus of FIG. 1 illustrating lateral tilting movement of the upper frame section relative to the pedestal about a longitudinal axis of the upper support frame.

Bearing portion 28 also includes a concave bearing surface 34 extending along a longitudinal axis 36 of the upper support frame 16 as shown in FIG. 3. Upper support frame 16 is coupled to a convex bearing surface 38 configured to engage bearing surface 34 and permit rotation of the upper support frame 16 about axis 36 to provide lateral tilting of the upper support frame 16 to the dotted positions shown in FIG. 3. Appropriate cylinders, gears, or other drive mechanisms (not shown) are used to provide powered lateral rotational movement of the upper support frame 16 about axis 36.

Referring again to FIG. 1, the surgical table apparatus 10 includes mattress sections 40 located on each of the upper frame sections 18, 20, 22, and 24 to support a patient. Mattress sections 40 can be any type of support surface including foam, air, gel, liquid, air fluidized or other support material.

Details of another suitable mattress or support surface for use on upper support frame 16 are disclosed in U.S. application Ser. No. 09/188,785, entitled SURGICAL TABLE, filed Nov. 6, 1998 which is incorporated herein by reference. Details of a controller for the mattress or support surface and the surgical table apparatus 10 are disclosed in U.S. application Ser. No. 09/187,825, entitled MEDICAL EQUIPMENT CONTROLLER, filed Nov. 6, 1998 which is also incorporated herein by reference.

Various types of head support sections 18 will be discussed in detail below with reference to FIGS. 14–21. Back frame section 20 is pivotably coupled to seat frame section 22 about transverse pivot axis 44. Leg support 24 includes a first frame section 46 pivotably coupled to seat section 22 about pivot axis 48. A second leg frame section 50 is pivotably coupled to section 46 about pivot axis 52. Separate mattress portions 40 are located above the first leg frame section 46 and the second leg frame section 50. Accessory rails 54 are mounted to various frame sections 20, 22, 46, 50 of upper support frame 16. Leg support 24 is extendable relative to the seat section 22 by extendable arms located between the first frame section 46 and the seat frame section 22 or between the first and second frame sections 46 and 50. In addition, leg support 24 is removable from the seat section by the caregiver without the use of tools as discussed below.

Figure 4:
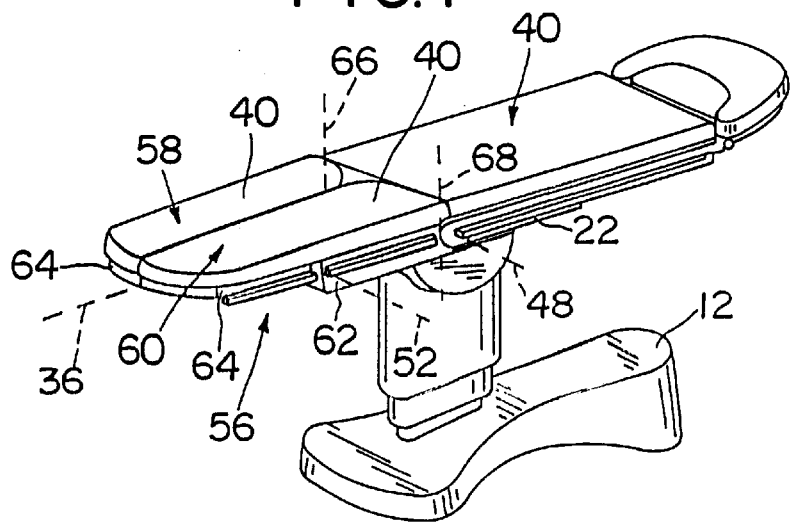
FIG. 4 is a perspective view of another embodiment of the present invention including a two-piece leg support split along a longitudinal axis of the upper frame section.
Figure 5:
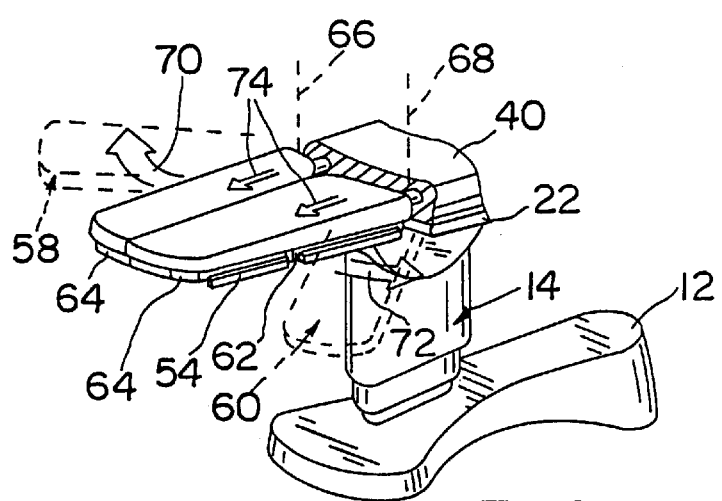
FIG. 5 is a perspective view similar to FIG. 4 illustrating movement of the first and second leg support sections relative to the remainder of the upper support frame.

FIGS. 4 and 5 illustrate another embodiment of a leg support 56. Those numbers referenced by numbers in FIGS. 1–3 perform the same or similar function. In the embodiment shown in FIGS. 4 and 5, the leg support 56 is a two-piece support including separate leg support sections 58 and 60 which are split along the longitudinal axis 36 of the upper support frame 16. Each of the first and second leg support sections 58 and 60 include first frame member 62 pivotably coupled to seat frame section 22 about pivot axis 48. Second leg frame sections 64 are pivotably coupled to first frame sections 62 about pivot axis 52. First and second leg sections 58 and 60 are also pivotable outwardly about a first axis 66 and a second axis 68, respectively, as illustrated by arrows 70 and 72 in FIG. 5. Therefore, first and second leg support sections 58 and 60 can be pivoted outwardly relative to the remainder of upper support frame 16 as illustrated by the dotted line positions 58 and 60 in FIG. 5. First and second leg support sections 58 and 60 also include telescoping portions which slide into the seat frame section 22 and permit the first and second leg sections 60 to be moved in the direction of arrows 74 to lengthen the leg support section 56. First and second leg support sections 58 and 60 removable as discussed below.

Figure 6:
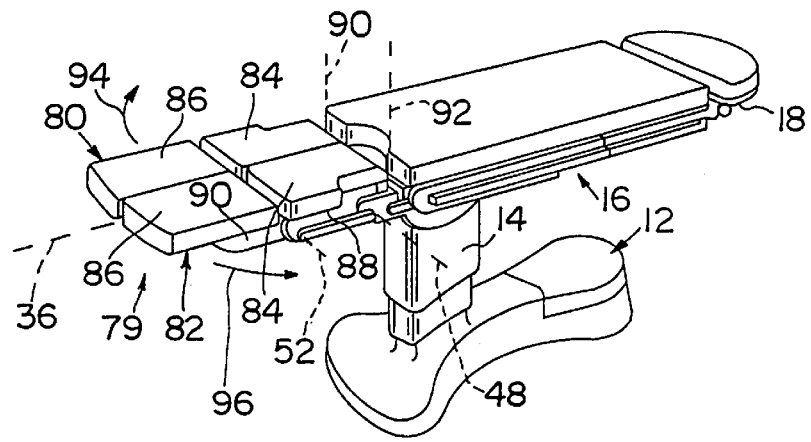
FIG. 6 is a perspective view of another embodiment of the present invention including a two-piece, two section leg support.

FIG. 6 illustrates another embodiment of the present invention in which the surgical table apparatus 10 includes a two-piece, two section leg support 79 having first and second leg support sections 80 and 82 split along longitudinal axis 36. Each of the first and second leg support sections 80 and 82 includes a first frame section 38 pivotably coupled to the seat section about pivot axis 48. A second frame section 90 is pivotably coupled to first frame section 88 about pivot axis 52. In addition, first and second leg support sections 80 and 82 are pivotably coupled to seat section 22 about vertical pivot axes 90 and 92, respectively, as discussed in detail below. Therefore, first and second leg support sections 80 and 82 can pivot outwardly in the direction of arrows 94 and 96, respectively, similar to leg sections 58 and 60 shown in FIGS. 4 and 5.

Figure 7:
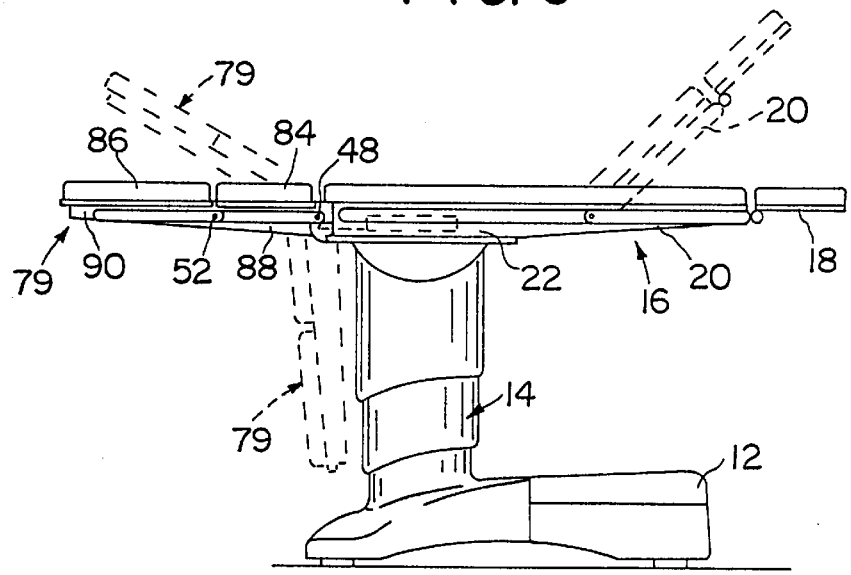
FIG. 7 is a side elevational view illustrating pivoting movement of the leg support sections of the surgical table apparatus about a first pivot axis and illustrating pivotal movement of a head frame section of the upper support frame.

Articulation of the leg supports 24, 56, and 79 of the present invention is illustrated in detail with reference to FIGS. 7–10. The FIG. 6 embodiment is used to illustrate pivotable movement of the leg supports 24, 56, and 79. FIG. 7 also illustrates upward pivotal movement of the head frame section 20 relative to the seat frame section 22.

Figure 8:
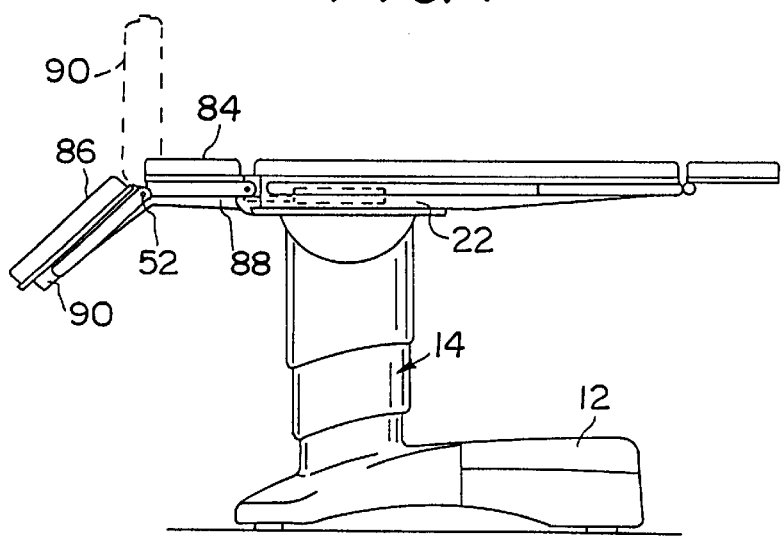
FIG. 8 is a side elevational view similar to FIG. 7 illustrating pivotal movement of the leg support sections about a second pivot axis.

Each of the leg supports 24, 56, and 79 can pivot about the first transverse pivot axis 48 through range of motion of +/−90°. Illustrated movement of leg section 79 about pivot axis 48 is shown in FIG. 7. Each of the leg supports 24, 56, and 79 can also pivot about the second transverse pivot axis 52 through a range of motion of +/−90° relative to the adjacent frame section. Illustrative movement of frame members 90 of foot section 79 relative to frame members 88 is shown in FIG. 8 When pivoted upwardly to the dotted line position of FIG. 8, frame member 90 may be used as a foot prop for the patient. It is understood that foot frame sections 50 and 64 of leg supports 24 and 56, respectively, can also pivot in a manner similar to FIG. 8 about pivot axis 52.

Figure 9:
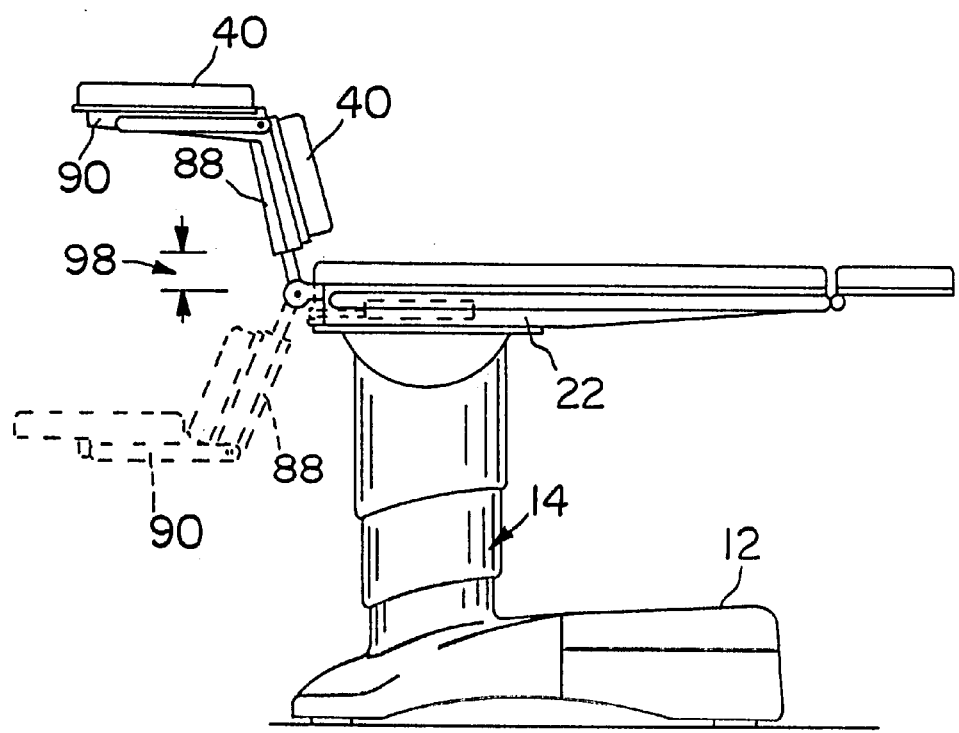
FIG. 9 illustrates further pivotal movement of the leg support sections relative to the remainder of the upper support frame.
Figure 10:
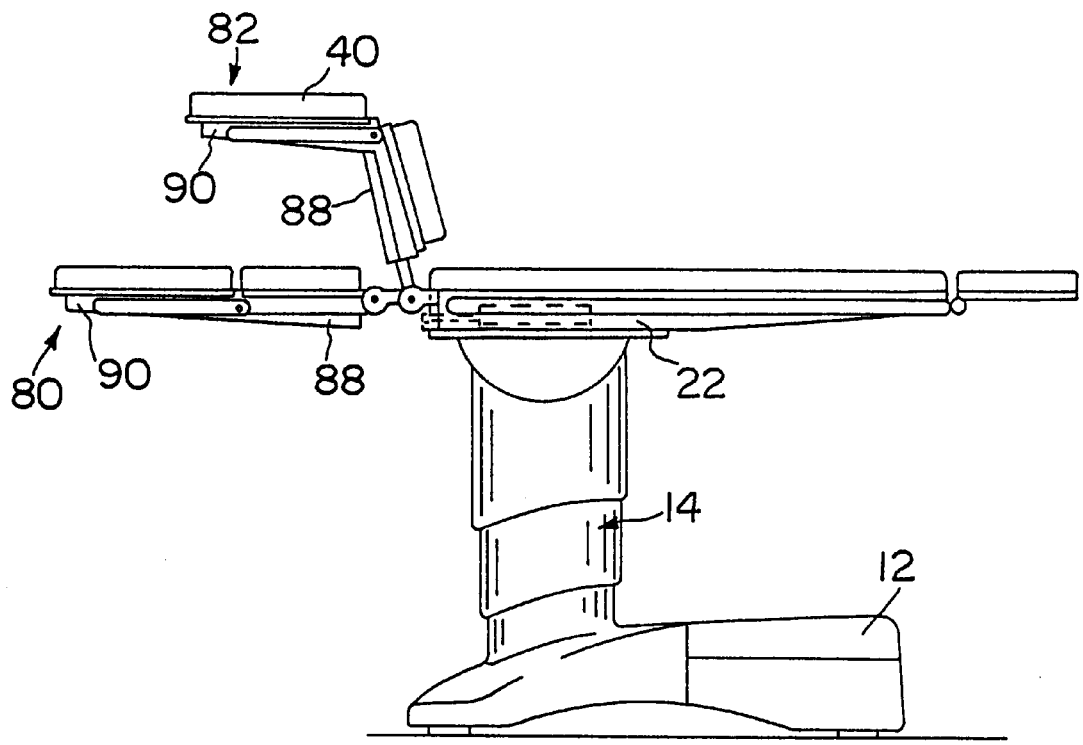
FIG. 10 illustrates independent pivotal movement of the two-piece leg support sections of the surgical table apparatus.

FIG. 9 illustrates another possible configuration for leg supports 24, 56, and 79. Since the separate frame members 88 and 90 of leg support section 79 are independently pivotable, the leg section can assume numerous desired configurations depending on a particular surgical procedure. FIG. 10 illustrates the first and second leg support sections 80 and 82 of leg support 79 in different configurations. The embodiments in FIGS. 4-6 can assume different orientations with each leg support section 58, 60 or 80, 90 since these leg support sections are independently adjustable. FIG. 9 also illustrates that first and second leg support sections are extendable as illustrated by dimension 98 as discussed in detail below.

Figure 11:
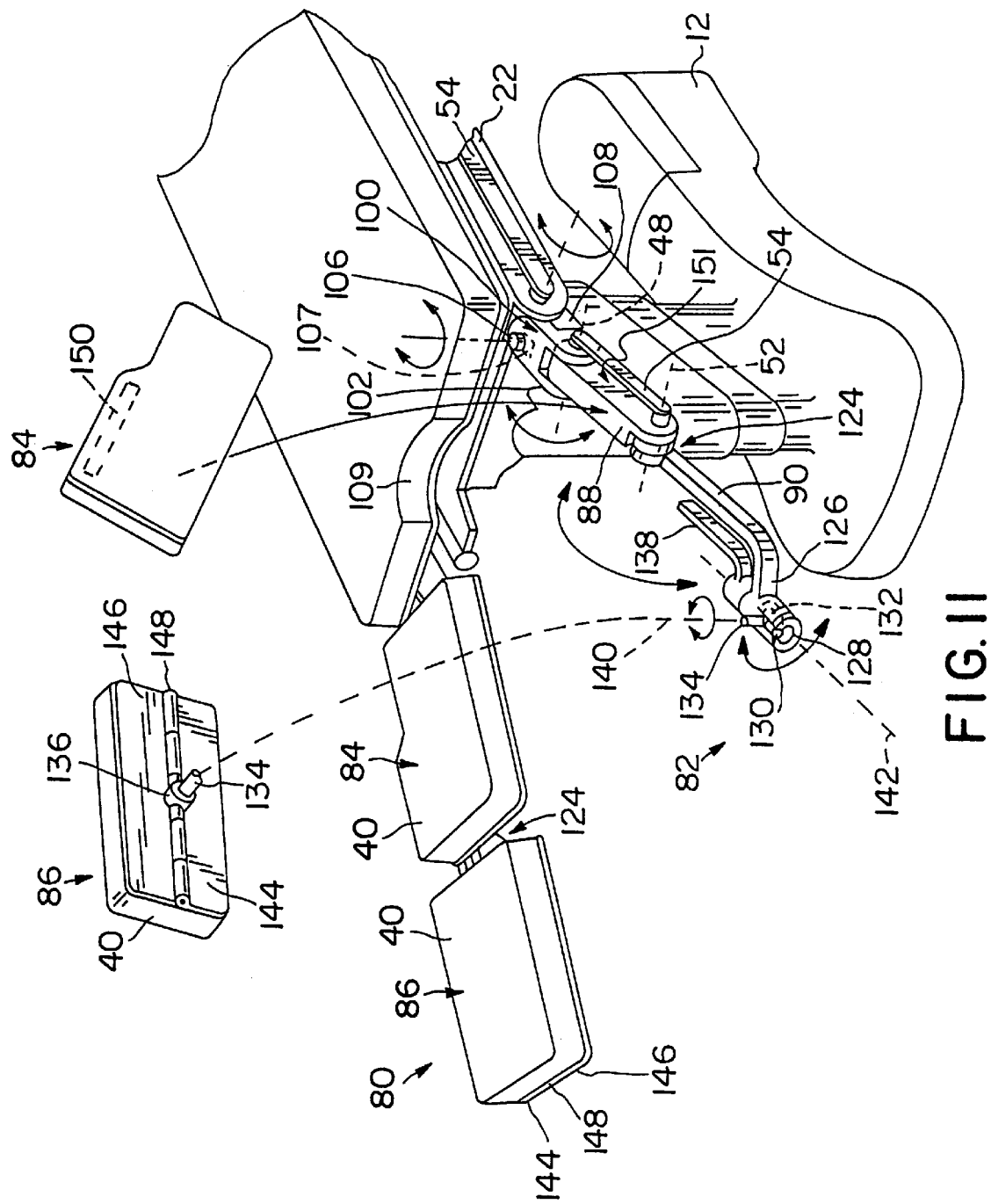
FIG. 11 is a perspective view illustrating further details of the leg support sections of the embodiment of FIG. 6.
Figure 12:
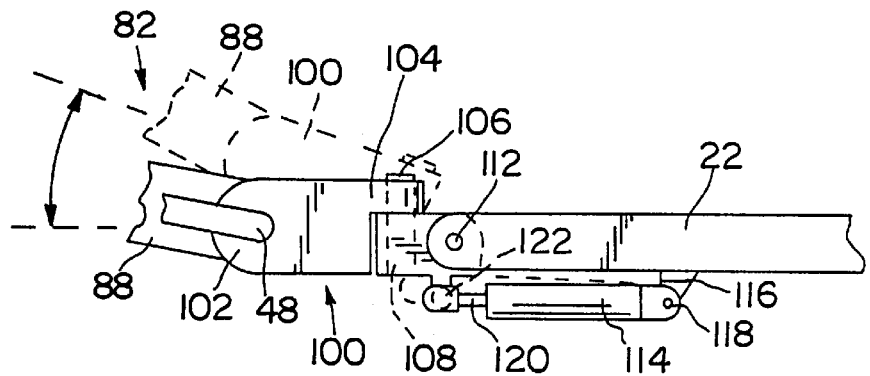
FIG. 12 is a side elevational view illustrating additional details of a linkage for coupling the leg support sections of FIG. 11 to the upper support frame.
Figure 13:
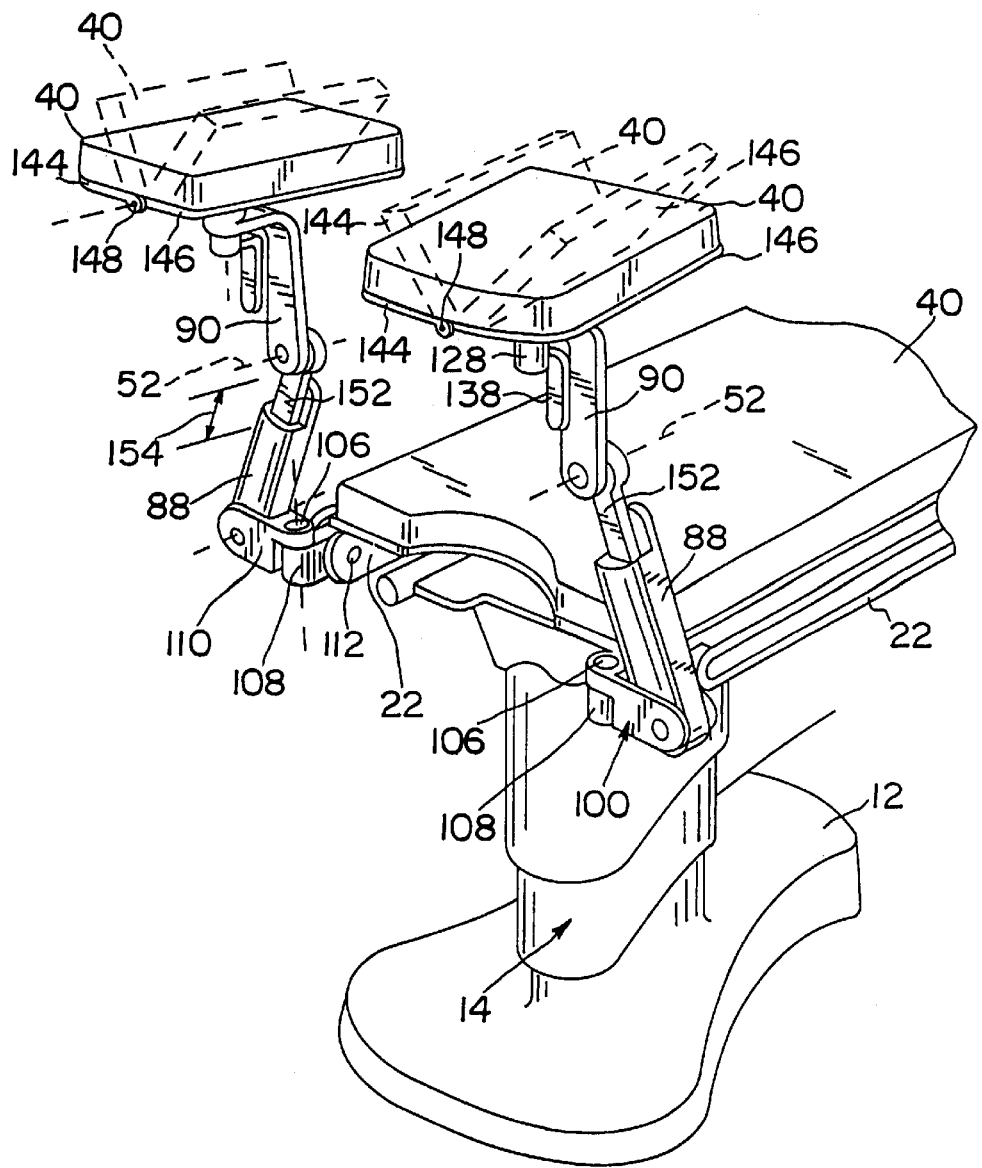
FIG. 13 illustrates the leg support sections of FIG. 11 pivoted upwardly into urology and OB/GYN leg support positions.

Further details of the leg support 79 are illustrated in FIGS. 11–13. As best shown in FIGS. 11 and 12, first frame section 88 is pivotably coupled to a clevis 100 about axis 48. The clevis 100 has spaced-apart side flanges 102 configured to receive an end of the frame section 88 for pivotably coupling the frame section 88 member to the clevis 100. As best shown in FIG. 12, clevis 100 further includes a mounting portion 104 having an aperture configured to receive a post 106 extending upwardly from coupler 108. Latches 107 actuatable by a caregiver without the use of tools are provided to secure the coupler 108 to the clevis 100. Therefore, leg support sections 80, 82 are easily removable for replacement with other leg supports 24 or 56 or for better access to end 109 of seat section 22 for access to the patient.

Coupler 108 is pivotably coupled to the seat frame section 22 about pivot connection 112. A cylinder 114 is pivotably coupled to a flange 116 extending from seat frame section 22 by pivot connection 118. A piston 120 is pivotably coupled to coupler 108 by pivot connection 122. Piston 120 is movable from a retracted position shown in solid lines in FIG. 12 to an extended position. In the extended position, the piston moves the coupler 108, the clevis 100, and the leg frame section 88 upwardly to the dotted position shown in FIG. 12 to elevate the leg support section 82 relative to the seat support section 22. In another embodiment, the coupler 108 is coupled to an arm member which is slidably received within an aperture of seat frame section 22 to permit the entire leg support section 82 to slide inwardly and outwardly relative to the seat support section 22 to lengthen the leg support section 82.

Frame member 88 is pivotably coupled to frame member 90 by joint connection 124. Joint connection 124 is either articulated by a piston and cylinder arrangement similar to FIG. 12 or is manually operable with a suitable joint 124 which is rigid enough to support the patient. All the joint connections of the present invention may be any suitable clutch assembly or latch mechanism. The latch mechanisms may include separate mating portions including a plurality of teeth to permit the joint to be pivoted to a desired location and then held in that location by the joint. Frame member 90 may also be mounted to a separate arm which is slidably received in frame member 88 to permit the length of leg support section 79 to be further adjusted as discussed below with reference to FIG. 13.

Frame section 90 includes a curved portion 126 and a cylindrical end portion 128. Cylindrical end portion 128 includes a socket and slot 130 configured to receive a ball 132 therein. A post 134 coupled to ball 132, post 134 is also coupled to a connector 136 of foot support 86. Therefore, foot support 86 is pivotably coupled to the cylindrical portion. A handle 138 coupled to cylindrical portion 128 is configured to lock the ball 132 and post 134 in a desired orientation. The handle 138 is actuated either by movement toward frame section 90 or by rotational movement. The post 134 is rotatable about a first axis 140 when in the position of FIG. 11. The post 134 can also be rotated toward a foot end of the table 10 to lie within slot 130 and then rotate about axis 142.

The foot support 86 includes separate panels or portions 144 and 146 coupled together by a hinge or coupler 148 as illustrated in FIG. 11. A mattress portion 40 is located above both panels 144 and 146. Thigh panels 84 are coupled to frame sections 88 by connectors 150. Connector 150 may be any suitable connector such as a latch, clamp, etc. The connector 150 may also be a tab configured to enter the slot 151 formed between frame member 88 and accessory rail 54. The thigh panels 84 are removable so that the leg support sections 80 and 82 can be articulated upwardly as shown in FIG. 13 to urology and OB/GYN examination positions. The foot panels 86 are manually adjustable into folded positions shown in dotted lines in FIG. 13 to form concave calf supports.

FIG. 13 also illustrates a separate arm 152 pivotably coupled to frame member 90 about axis 52. The arm 152 is slidably received within frame member 88 so that the arm 152 may be extended to adjust the length of the leg support sections as illustrated by dimension 154.

In operation, the leg sections 80 and 82 may be manually or automatically moved to desired positions. When the leg sections 80 and 82 are moved upwardly to the position of FIG. 13, handle actuator 138 is actuated to release the ball 132 and permit the ball 132 to be rotated within slot 130 so that the post 134 extends upwardly to provide the calf supports.

The removable leg supports 24, 56 and 79 provide a flexible surgical table apparatus 10 which can be modified by a caregiver as desired quickly and easily without the use of separate tools. Leg supports 24, 56 and 79 are removable to expose the end 109 of seat section 20 to provide better access to the patient during certain medical procedures. In addition, the removable leg supports 24, 56 and 79 permit the leg supports 24, 56 and 79 to be interchangeable on the of the surgical table apparatus 10. The removable leg supports 24, 56 and 79 also permit attachment of special orthopaedic frames to the seat frame section 22 for orthopedic surgery. Each of the leg supports 24, 56 and 79 includes an arm and a support coupled to the arm.

Each of the leg supports 24, 56 and 79 is also length adjustable relative to the seat frame section 22. This permits flexibility of the caregiver in positioning the leg supports 24, 56 and 79 at a desired location to align the patient in a desired position for a surgical procedure. Since the leg supports 24, 56, and 79 are all pivotable about two pivot axes 48, 52, the leg supports 24, 56, and 79 can be articulated to provide a knee shelf for the patient in a prone position without requiring separate components to be attached to the upper support frame 16. In addition, a foot prop position and a knee gatch position are easily obtainable by the leg supports 24, 56, and 79 without separate attachments.

Figure 16:
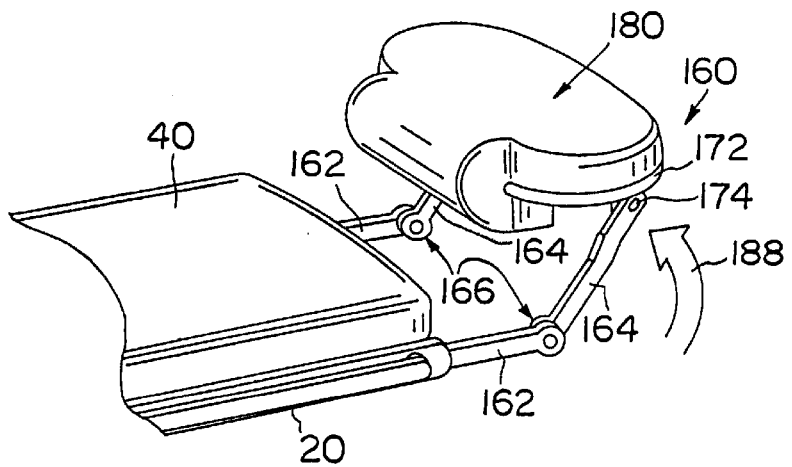
FIG. 16 is a perspective view illustrating the head support pivoted upwardly to provide support for a side of a patient's head.
Figure 17:
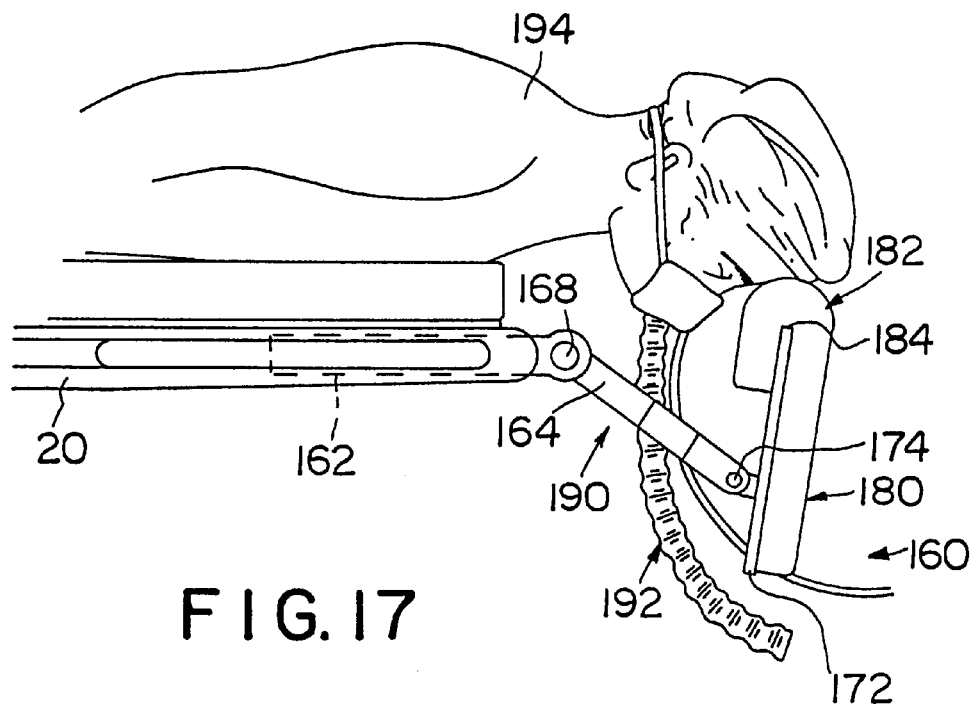
FIG. 17 illustrates pivotal movement of the head support to provide a head support for a patient in a supine position or an airway access head support for a patient in a prone position.

FIGS. 14–17 illustrate a one-piece head support 160 of the present invention. Head support 160 includes a pair of spaced-apart arms 162 which are received within slots formed in head frame section 20. Arms 162 are pivotably coupled to a second pair of arms 164 by joints 166 so that arms 162 and 164 can pivot about pivot axis 168 as shown by doubleheaded arrow 170 in FIG. 14. A bottom plate 172 is pivotably coupled to arms 164 by joint connections 174. Therefore, plate 172 can pivot relative to arms 164 about axis 176 as illustrated by doubleheaded arrow 178 in FIG. 14. A pad section 180 is located over plate 172. A U-shaped portion 182 of pad 180 extends around an end edge 184 of plate 172 as best illustrated in FIGS. 16 and 17.

Figure 14:
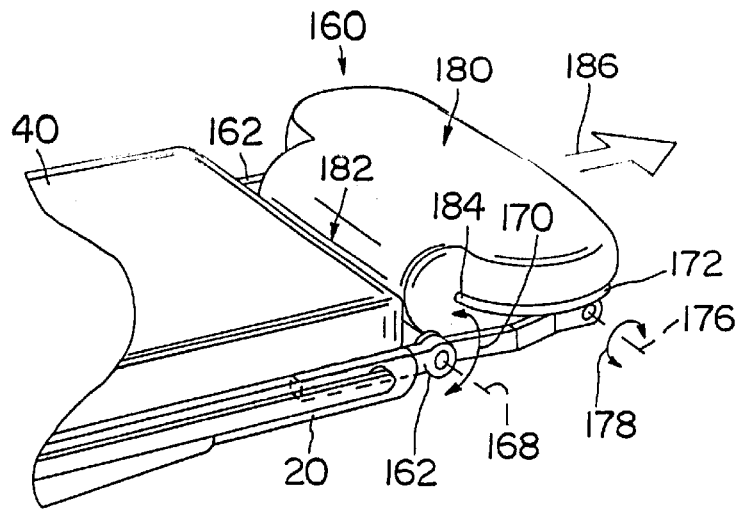
FIG. 14 is a perspective view illustrating a one-piece head support of the present invention.
Figure 15:
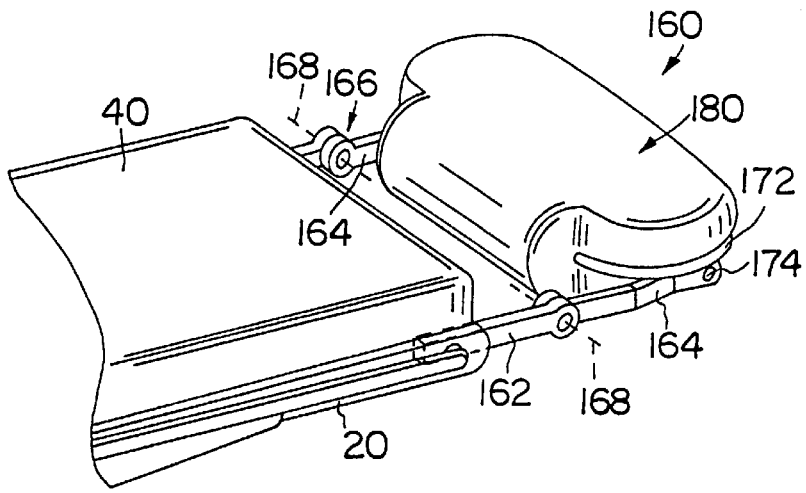
FIG. 15 is a perspective view similar to FIG. 14 illustrating movement of the head support to adjust the length of the head support.

The head support 160 is movable to a plurality of different positions relative to the back frame section 20 to support the head and neck of a patient. A first position is shown in FIG. 14 to provide head and neck support. Arms 162 may be extended from the slots in head frame section 20 in the direction of arrow 186 in FIG. 14 to an extended position shown in FIG. 15. Head support 160 is also removable from head frame section 20. Arms 164 are also pivotable upwardly in the direction of arrow 188 in FIG. 16 to raise the pad 180 to a height above the level of mattress 40 on head frame section 20. In the FIG. 16 configuration, head support 160 provides lateral support for a side of the patient's head when a patient is positioned on one side or another on the mattress 40.

Head support 160 is also pivotable to the position shown in FIG. 17 to provide support for the patient's head only. The patient's head can rest on the U-shaped portion of the pad in either a supine position or a prone position as shown in FIG. 17. In the prone position, an opening 190 is provided between the arms 164 and the plate 172 for airway access. Tubes or hoses 192 can be routed through the opening 190 to the patient 194.

The joint connections 166 and 174 include suitable clutch assemblies which have, for instance, Belleville washers or other mechanisms to hold the arms 162 and 164 and plate 172 at desired relative positions. It is understood that other types of locking mechanisms or latches may be used. In addition, movement of the arms 162 and 164 and plate 172 may be controlled by suitable automatic controls, such as by cylinder and piston arrangements if desired.

FIGS. 18–21 disclose a two-piece head support 200 of the present invention. Head support 200 includes an inner support section 202 and an outer U-shaped support section 204. Inner support section 202 includes an inner support plate 206, and outer support section 204 on an outer support plate 208. Head support 200 includes a pair of spaced apart arms 210 which are received within slots formed in head frame section 20. A pair of posts 212 are rotatably coupled to arms 210 by joints 214. Plate 206 is coupled to posts 212. Therefore, inner support section 202 is pivotably coupled to arms 210 by joints 214 about pivot axis 216. Arms 218 are pivotably coupled to the arms 210 by joints 214, independently of posts 212.

Therefore, arms 218 can independently rotate about pivot axis 216 separately from inner support section 202. Plate 208 of outer support section 204 is pivotably coupled to arms 218 by joints 220. Therefore, plate 208 can rotate about axis 222 relative to arms 218.

Figure 18:
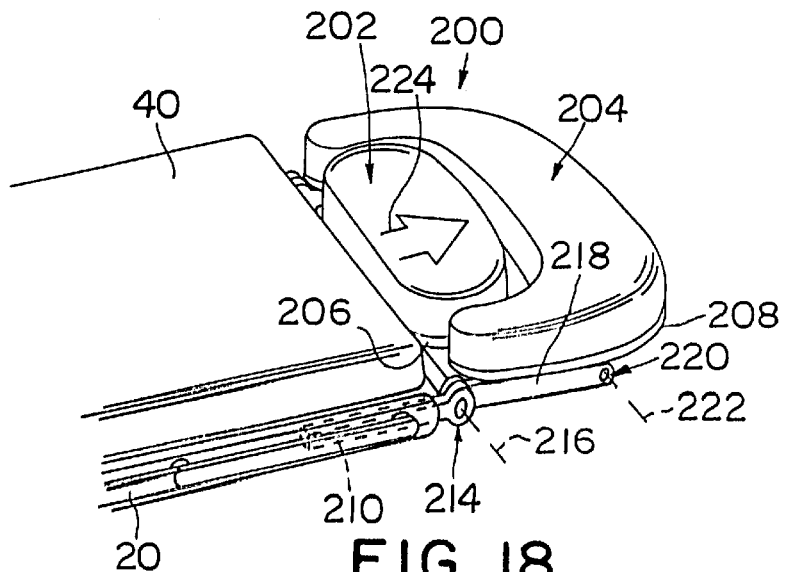
FIG. 18 is a perspective view of a two-piece head support of the present invention.
Figure 19:
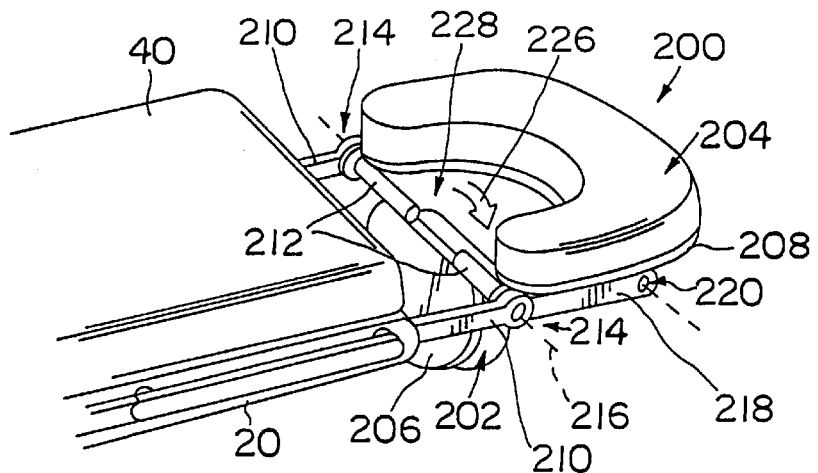
FIG. 19 illustrates movement of the head support to extend the length of the head support and pivotable movement of an inner support section to provide airway access when the patient is in a prone position.

In operation, two-piece head support 200 can be positioned as shown in FIG. 18 to provide both head and neck support for the patient. The entire head support 200 is movable outwardly in the direction of arrow 224 by moving the arms 210 to the extended position shown in FIG. 19. Head support 200 is also removable from upper support frame 20. Inner support section 202 is pivotable downwardly in the direction of arrow 226 in FIG. 19 to provide an opening 228 for airway access when a patient is in a prone position on the mattress 40. The patient's forehead is supported by the outer support section 204 in the prone position.

Figure 20:
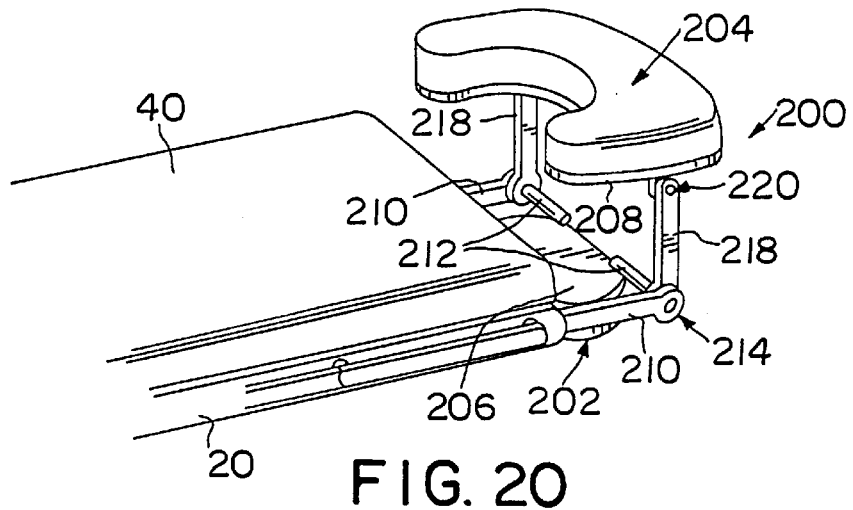
FIG. 20 is a perspective view illustrating an inner support section in a downwardly pivoted position and an outer support section in an upwardly pivoted position to provide lateral support for the side of a patient's head.

In another configuration, the inner support section 202 is pivoted downwardly out of the way as shown in FIG. 20. The second arms 218 and plate 208 are pivoted so that the outer support section 204 is elevated relative to the mattress portion 40 on head frame section 20. This provides lateral support for a side of a patient's head when the patient is located on one side or another on mattress 40.

Figure 21:
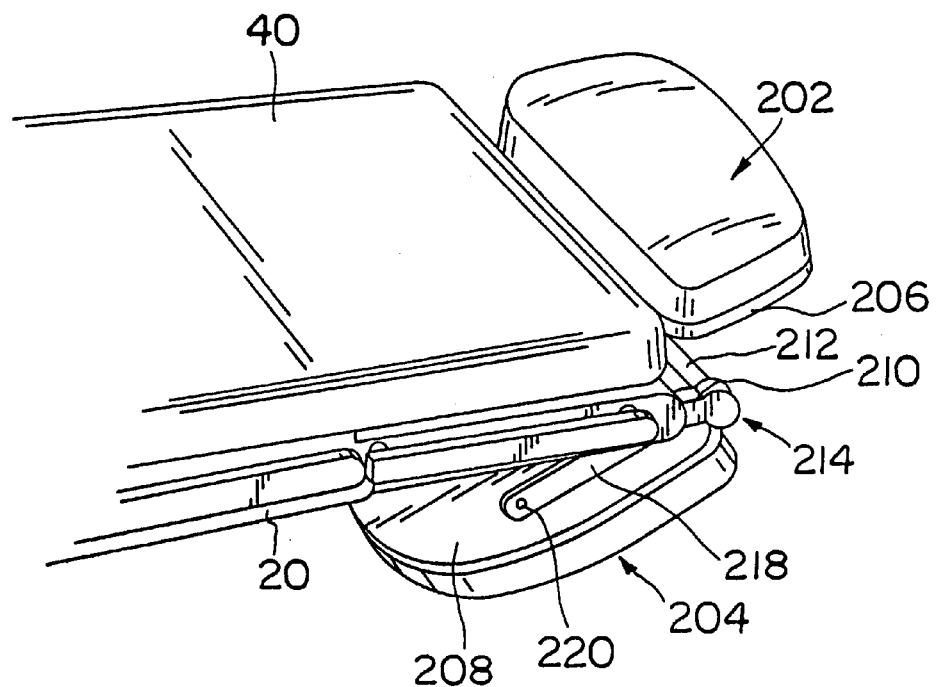
FIG. 21 is a perspective view illustrating the outer support section in a downwardly pivoted position so that the inner support section supports the patient's neck while providing full head access to the patient.

Finally, plate 208 and arms 218 are pivotable to the position shown in FIG. 21. In this position, inner support section 202 provides support for a patient's neck while providing fill head access to the patient during a procedure.

The joint connections 214 and 220 include suitable clutch assemblies which have, for instance, Belleville washers or other mechanisms to hold the position of arms 214 and 220, posts 212 and plate 208 at desired relative positions. It is understood that other types of locking mechanisms or latches may be used. In addition, movement of the arms 210 and 218, rods 212 and plate 208 may be controlled by suitable automatic controls, such as by cylinder and piston arrangements.

Although the embodiments illustrated in FIGS. 15-21 illustrate a pair of arms 162, 164, 210, and 218, it is understood that single arms may be used to support the head supports 160, 200. The arm coupled to the plates 172 and 208 may be a single piece curved yoke attached to opposite sides of the plate, if desired.

Although the invention has been described in detail with reference to a certain illustrated embodiment, variations and modifications exist within the scope and spirit of the invention as described and as defined in the following claims.

What is claimed is:

1. A surgical table apparatus comprising a base and an upper support frame coupled to the base, the upper support frame including a head frame section, a seat frame section, and first and second separate leg support sections, the first and second leg support sections each including a first frame section pivotally coupled to the seat frame section by a first joint for independent movement about a first pivot axis, and a second frame section pivotally coupled to the first frame section by a second joint for independent movement about a second pivot axis, the first and second pivot axes being transverse to a longitudinal axis of the upper support frame, the first joint of each of the first and second leg support sections including a clevis pivotably coupled to the first frame section, and a coupler pivotably coupled to the clevis about a pivot axis transverse to the first pivot axis, the coupler being pivotally coupled to the seat frame section.

2. The apparatus of claim 1, further comprising a cylinder having a movable piston to control pivotable movement of the first frame section relative to the seat frame section, one of the cylinder and piston being pivotably coupled to the seat frame section, and the other of the cylinder and piston being pivotably coupled to the coupler.

3. A surgical table apparatus comprising a base and an upper support frame coupled to the base, the upper support frame including a head frame section, a seat frame section, and first and second separate leg support sections, the first and second leg support sections each including a first frame section pivotally coupled to the seat frame section by a first joint for independent movement about a first pivot axis, and a second frame section pivotably coupled to the first frame section by a second joint for independent movement about a second pivot axis, the first and second pivot axes being transverse to a longitudinal axis of the upper support frame, each of the first and second leg support sections including a foot support panel pivotably coupled to the second frame section, each of the first and second leg support sections including a selectively removable thigh support panel coupled to the first frame section.

4. A surgical table apparatus comprising a base and an upper support frame coupled to the base, the upper support frame including a head frame section, a seat frame section, and first and second separate leg support sections, the first and second leg support sections each including a first frame section pivotally coupled to the seat frame section by a first joint for independent movement about a first pivot axis, and a second frame section pivotably coupled to the first frame section by a second joint for independent movement about a second pivot axis, the first and second pivot axes being transverse to a longitudinal axis of the upper support frame, each of the first and second leg support sections including a foot support panel pivotably coupled to the second frame section, each foot support panel being coupled to a ball connector and each second frame section being formed to include a socket configured to receive the ball so that the foot support panel is movable relative to the second frame section.

5. The apparatus of claim 4, wherein each of the first and second leg support sections includes an actuator coupled to the second frame section to release the ball for pivotable movement relative to the second frame section.

6. A surgical table apparatus comprising a base and an upper support frame coupled to the base, the upper support frame including a head frame section, a seat frame section, and first and second separate leg support sections, the first and second leg support sections each including a first frame section pivotally coupled to the seat frame section by a first joint for independent movement about a first pivot axis, and a second frame section pivotably coupled to the first frame section by a second joint for independent movement about a second pivot axis, the first and second pivot axes being transverse to a longitudinal axis of the upper support frame, each of the first and second leg support sections including a foot support panel pivotably coupled to the second frame section, each foot support panel including a bottom plate having first and second separate sections pivotably coupled together so that the foot support panels are foldable to form generally concave calf supports.

7. The apparatus of claim 6, wherein the first joint of each of the first and second leg support sections includes an arm movably coupled to the seat frame section to permit a length of the first and second leg support sections to be adjusted relative to the seat frame section.

8. A surgical table apparatus comprising a base and an upper support frame coupled to the base, the upper support frame including a head frame section, a seat frame section, and first and second separate leg support sections, the first and second leg support sections each including a first frame section pivotally coupled to the seat frame section by a first joint for independent movement about a first pivot axis, and a second frame section pivotably coupled to the first frame section by a second joint for independent movement about a second pivot axis, the first and second pivot axes being transverse to a longitudinal axis of the upper support frame, each second joint including a third frame section pivotally coupled to the second frame section, the third frame section being slidably coupled to the first frame section to permit the position of the second frame section to be adjusted relative to the first frame section.

9. The apparatus of claim 8, wherein the seat frame section includes first and second side portions, and the first and second leg support sections are pivotable outwardly relative to the seat frame section about first and second vertical pivot axes located adjacent the first and second side portions of the seat frame section, respectively.

10. The apparatus of claim 8, further comprising first and second separate mattress sections located on the first and second leg support sections, respectively.

11. The apparatus of claim 8, wherein the first frame section of each of the first and second leg support sections is pivotable relative to the seat frame section through a range of motion of +/−90° relative to the seat frame section.

12. The apparatus of claim 11, wherein the second frame section of each of the first and second leg support sections is pivotable relative to the first frame section through a range of motion of +/−90°.

13. The apparatus of claim 8, wherein each of the first and second leg support sections includes a foot support panel pivotably coupled to the second frame section.

14. The apparatus of claim 8, wherein each of the first joints includes a latch configured to secure the first frame section to the seat frame section, the latch being releasable to permit the first and second leg support sections to be removed from the seat frame section.

15. A surgical table apparatus comprising a base, and an upper support frame coupled to the base, the upper support frame including head frame section, a seat frame section, and a leg support movably coupled to the seat frame section to permit a length of the leg support to be adjusted relative to the seat frame section the leg support including a first frame section pivotally coupled to the seat frame section by a first joint or movement about a first pivot axis, and a second frame section pivotably coupled to the first frame section by a second joint for movement about a second pivot axis, the first and second pivot axes being transverse to a longitudinal axis of the upper support frame, the first joint including an arm movably coupled to the seat frame section to permit a length of the leg support to be adjusted relative to the seat frame section, the first frame section being pivotably coupled to the arm.

16. The apparatus of claim 15, wherein the first frame section is pivotable relative to the seat frame section through a range of motion of +/−90° relative to the seat frame section.

17. The apparatus of claim 16, wherein the second frame section is pivotable relative to the first frame section through a range of motion of +/−90°.

18. The apparatus of claim 15, further comprising a cylinder having a movable piston to control pivotable movement of the first frame section relative to the seat frame section, one of the cylinder and piston being pivotably coupled to the seat frame section, and the other of the cylinder and piston being pivotably coupled to the first frame section.

19. The apparatus of claim 15, wherein the first joint includes a latch configured to secure the first frame section to the seat frame section, the latch being releasable to permit the leg support to be removed from the seat frame section.

20. A surgical table apparatus comprising a base and an upper support frame coupled to the base, the upper support frame including a head frame section, a seat frame section, and first and second separate leg support sections, the first and second leg support sections each including a first frame section pivotally coupled to the seat frame section by a first joint for independent movement about a first pivot axis, and a second frame section pivotally coupled to the first frame section by a second joint for independent movement about a second pivot axis, the first and second pivot axes being transverse to a longitudinal axis of the upper support frame, the second joint including a third frame section pivotally coupled to the second frame section, the third frame section being slidably coupled to the first frame section to permit the position of the second frame section to be adjusted relative to the first frame section.

21. A surgical table apparatus having a longitudinal axis, the apparatus comprising
a seat section, and
first and second leg support sections, each of the first and second leg support sections including an arm coupled to the seat section and a support coupled to the arm, the support including first and second portions and a coupler that permits relative movement of the first and second portions about an axis substantially parallel to the longitudinal axis.

22. The apparatus of claim 21, wherein each of the first and second leg support sections further includes a selectively removable thigh support.

23. The apparatus of claim 21, wherein each support is coupled to a ball connector and each arm is formed to include a socket configured to receive the ball so that the support is movable relative to the arm.

24. The apparatus of claim 23, wherein each of the first and second leg support sections includes an actuator coupled to the arm to release the ball for pivotable movement relative to the arm.

25. The apparatus of claim 21, wherein the first and second portions of the support are pivotably coupled together and foldable to form generally concave calf supports.

26. The apparatus of claim 21, wherein each arm includes first, second, and third portions, the third portion is pivotably coupled to one of the first and second portions, and the third portion is slidably coupled to one of the first and second portions of the arm to permit the position of the second portion of the arm to be adjusted relative to the first portion of the arm.

27. The apparatus of claim 21, wherein each of the arms includes first and second portions and a coupler configured to permit the first portion of the arm to move axially relative to the second portion of the arm.

28. The apparatus of claim 21, wherein the arm of each of the first and second leg support sections includes a first frame section pivotably coupled to the seat section by a first joint for independent movement about a first pivot axis and a second frame section pivotably coupled to the first frame section by a second joint for independent movement about a second pivot axis, each second joint includes a third frame section pivotably coupled to the second frame section, and the third frame section being slidably coupled to the first frame section to permit the position of the second frame section to be adjusted relative to the first frame section.

29. The apparatus of claim 21, wherein the apparatus further includes an upper surface, each of the first and second leg support sections includes a coupler configured to couple the support to the arm, the arm is configured to be positioned in a first position wherein the arm extends along an axis that is substantially parallel to the upper surface and a second position wherein the arm extends along an axis that intersects a plane defined by the upper surface, the coupler is configured to position the support substantially parallel to the upper surface when the arm is in its first and second positions.

30. The apparatus of claim 21, wherein the arm of the first and second leg support sections include a first frame section that includes first and second portions, a first coupler configured to pivotably couple the first portion to the seat section, a second frame section, a second coupler configured to pivotably couple the second frame section to the first frame section, and a third coupler configured to permit relative axial movement of the first and second portions of the first frame section.

31. A surgical table apparatus having a longitudinal axis, the apparatus comprising
a seat section, and
first and second leg support sections, each of the first and second leg support sections including an arm coupled to the seat section and a support coupled to the arm, the support including an upwardly-facing surface movable between a substantially flat position and a substantially longitudinally-extending concave position.

32. The apparatus of claim 31, wherein each of the first and second leg support sections further includes a selectively removable thigh support.

33. The apparatus of claim 31, wherein each support is coupled to a ball connector and each arm is formed to include a socket configured to receive the ball so that the support is movable relative to the arm.

34. The apparatus of claim 33, wherein each of the first and second leg support sections includes an actuator coupled to the arm to release the ball for pivotable movement relative to the arm.

35. The apparatus of claim 31, wherein each arm includes first, second, and third portions, the third portion is pivotably coupled to one of the first and second portions, and the third portion is slidably coupled to one of the first and second portions of the arm to permit the position of the second portion of the arm to be adjusted relative to the first portion of the arm.

36. The apparatus of claim 31, wherein each of the arms includes first and second portions and a coupler configured to permit the first portion of the arm to move axially relative to the second portion of the arm.

37. The apparatus of claim 31, wherein the arm of each of the first and second leg support sections includes a first frame section pivotably coupled to the seat section by a first joint for independent movement about a first pivot axis and a second frame section pivotably coupled to the first frame section by a second joint for independent movement about a second pivot axis, each second joint includes a third frame section pivotably coupled to the second frame section, and the third frame section being slidably coupled to the first frame section to permit the position of the second frame section to be adjusted relative to the first frame section.

38. The apparatus of claim 31, wherein the apparatus further includes an upper surface, each of the first and second leg support sections includes a coupler configured to couple the support to the arm, the arm is configured to be positioned in a first position wherein the arm extends along an axis that is substantially parallel to the upper surface and a second position wherein the arm extends along an axis that intersects a plane defined by the upper surface, the coupler is configured to position the support substantially parallel to the upper surface when the arm is in its first and second positions.

39. The apparatus of claim 31, wherein the arm of the first and second leg support sections include a first frame section that includes first and second portions, a first coupler configured to pivotably couple the first portion to the seat section, a second frame section, a second coupler configured to pivotably couple the second frame section to the first frame section, and a third coupler configured to permit relative axial movement of the first and second portions of the first frame section.

40. A surgical table apparatus comprising a seat section, and first and second leg support sections, each of the first and second leg support sections including an arm coupled to the seat section, a connector, a first support being one of coupled to the arm by the connector or removed from the arm, and a second support coupled to the arm, the second support including an upwardly-facing surface movable between a substantially flat position and a substantially concave position.

41. The apparatus of claim 40, wherein the arm of each of the first and second leg support sections includes a first frame section pivotally coupled to the seat section by a first joint for independent movement about a first pivot axis and a second frame section pivotally coupled to the first frame section by a second joint for independent movement about a second pivot axis, each second joint includes a third frame section pivotally coupled to the second frame section, and the third frame section being slidably coupled to the first frame section to permit the position of the second frame section to be adjusted relative to the first frame section.

42. The apparatus of claim 40, wherein the apparatus further includes an upper surface, each of the first and second leg support sections includes a coupler configured to couple the second support to the arm, the arm is configured to be positioned in a first position wherein the arm extends along an axis that is substantially parallel to the upper surface and a second position wherein the arm extends along an axis that intersects a plane defined by the upper surface, the coupler is configured to position the second support substantially parallel to the upper surface when the arm is in its first and second positions.

43. The apparatus of claim 40, wherein the arm of the first and second leg support sections include a first frame section that includes first and second portions, a first coupler configured to pivotably couple the first portion to the seat section, a second frame section, a second coupler configured to pivotably couple the second frame section to the first frame section, and a third coupler configured to permit relative axial movement of the first and second portions of the first frame section.

44. The apparatus of claim 40, wherein the first support is positioned adjacent to the seat frame section when the first support is coupled to the arm.

45. The apparatus of claim 40, wherein each of the arms includes first and second portions and a coupler configured to permit the first portion of the arm to move axially relative to the second portion of the arm.

46. The apparatus of claim 40, wherein each of the first and second supports is coupled to a ball connector and each arm is formed to include a socket configured to receive the ball so that the first support is movable relative to the arm.

47. The apparatus of claim 46, wherein each of the first and second leg support sections includes an actuator coupled to the arm to release the ball for pivotable movement relative to the arm.

48. The apparatus of claim 40, wherein each first support includes a bottom plate having first and second separate sections pivotably coupled together so that the first supports are foldable to form generally concave calf supports.

49. The apparatus of claim 40, wherein each arm includes first, second, and third portions, the third portion is pivotably coupled to one of the first and second portions, and the third portion is slidably coupled to one of the first and second portions of the arm to permit the position of the second portion of the arm to be adjusted relative to the first portion of the arm.

50. A surgical table apparatus comprising a seat section, and first and second leg support sections, each of the first and second leg support sections including an arm coupled to the seat section, the arm including first and second portions and a support coupled to the second portion of the arm, a first coupler being configured to permit the first portion to move axially relative to the second portion, and second and third couplers configured to permit the support to rotate relative to the seat frame section.

51. A surgical table apparatus comprising a seat section, and first and second leg support sections, each of the first and second leg support sections including an arm coupled to the seat section and a support coupled to the arm, the arm including a first frame section pivotally coupled to the seat section by a first joint for independent movement about a first pivot axis, and a second frame section pivotably coupled to the first frame section by a second joint for independent movement about a second pivot axis, each second joint including a third frame section pivotably coupled to the second frame section, the third frame section being slidably coupled to the first frame section to permit the position of the second frame section to be adjusted relative to the first frame section.

52. A surgical table apparatus comprising a seat section, and first and second leg support sections, the first and second leg support sections including a first arm, the first arm including first and second sections, a first coupler configured to pivotally couple the first arm to the seat section, a second arm, a second coupler configured to pivotally couple the second arm to the first arm, and a third coupler configured to permit relative axial movement of the first and second sections of the first arm.

* * * * *